United States Patent
Yun et al.

(10) Patent No.: US 7,470,707 B2
(45) Date of Patent: Dec. 30, 2008

(54) CRYSTALLINE MONOHYDRATE CLOPIDOGREL NAPHTHALENEDISULFONATE AND PROCESS OF PREPARATION

(75) Inventors: Sangmin Yun, Seongnam-si (KR); Eun Sook Kim, Seoul (KR); Hee Seock Kim, Daejeon (KR); Bo Sung Kwon, Geoje-si (KR); Cheol Kyung Kim, Namyangju-si (KR); Han Kyong Kim, Yongin-si (KR); Kwee-Hyun Suh, Suwon-si (KR); Gwan Sun Lee, Seoul (KR)

(73) Assignee: Hanmi Pharm. Co., Ltd, Kyungki-do (KR)

( * ) Notice: Subject to any disclaimer, the term of this patent is extended or adjusted under 35 U.S.C. 154(b) by 262 days.

(21) Appl. No.: 10/971,028

(22) Filed: Oct. 25, 2004

(65) Prior Publication Data

US 2005/0228012 A1 Oct. 13, 2005

(30) Foreign Application Priority Data

Apr. 9, 2004 (KR) ............... 10-2004-0024361
Jun. 7, 2004 (KR) ............... 10-2004-0041309

(51) Int. Cl.
*C07D 495/04* (2006.01)
*A61K 31/4365* (2006.01)

(52) U.S. Cl. ................... 514/301; 546/114
(58) Field of Classification Search ............. 546/114; 514/301

See application file for complete search history.

(56) References Cited

U.S. PATENT DOCUMENTS

| 4,847,265 | A | 7/1989 | Badore et al. |
| 6,429,210 | B1 | 8/2002 | Bousquet et al. |
| 2005/0256152 | A1* | 11/2005 | Doser et al. ............. 514/301 |

FOREIGN PATENT DOCUMENTS

EP 0 281 459 A1 9/1988

OTHER PUBLICATIONS

Caplus English abstract JP 04128265, DN 117:212338, Izawa Toshio et al Apr. 1992.*
PharmaceuticalSalts ... Berge Stephen et al. 1977.*

* cited by examiner

*Primary Examiner*—Rita J Desai
(74) *Attorney, Agent, or Firm*—Sughrue Mion, PLLC (57) ABSTRACT

A crystalline clopidogrel naphthalenesulfonate or a hydrate thereof, a method for preparing same, and a pharmaceutical composition containing same are provided.

10 Claims, 8 Drawing Sheets

CRYSTALLINE MONOHYDRATE CLOPIDOGREL NAPHTHALENEDISULFONATE AND PROCESS OF PREPARATION

This is a utility application under 35 U.S.C. 1.111(a) which claims priority from Korean Patent Application 10-2004-0024361 filed on Apr. 9, 2004, and Korean Patent Application 10-2004-0041309 filed on Jun. 7, 2004, all of which are incorporated herein by reference.

FIELD OF THE INVENTION

The present invention relates to crystalline clopidogrel naphthalenesulfonate or hydrate thereof, a method for preparing same, and a pharmaceutical composition containing same.

BACKGROUND OF THE INVENTION

Clopidogrel (methyl(+)-(S)-α-(o-chlorophenyl)-6,7-dihydrothieno[3,2-a]pyridine-5(4H)-acetate), the compound of formula (II) is known as a useful medicament for the treatment and prevention of various platelet-associated vascular diseases such as stroke, cerebral arteriosclerosis, myocardial infarction, angina pectoris, arrhythmia, peripheral arteries disease, and Burger's disease (see European Patent No. 281,459 B1 and U.S. Pat. No. 4,847,265).

(II)

However, clopidogrel itself as free base form is an oil which is difficult to purify, and the ester group thereof liable to hydrolysis to produce the acid of formula (III) which has no biological activity. Also, under moist and heat conditions, it can be transformed to the levorotatory isomer of formula (IV) having much less pharmacological activity. Accordingly, there has been a need to convert clopidogrel to a crystalline form which is very stable and easily purifiable, and for the purpose, it is common to make an acid addition salt using a pharmaceutically acceptable inorganic or organic acid.

(III)

(IV)

European Patent No. 281,459 B1 and U.S. Pat. No. 4,847,265 disclose a number of acid addition salts of clopidogrel prepared using various inorganic or organic acids. However, it is described that most of these salts are amorphous, hygroscopic and/or low melting, which are improper to use in pharmaceutical composition. Even the claimed crystalline salts such as hydrochloride, hydrobromide, hydrogen sulfate and taurocholate, have some problems. The taurocholate is unsuitable for use as a pharmaceutically acid addition salt of clopidogrel because taurocholic acid itself has another pharmacological activity, i.e., bile secretion. Also it was confirmed by the inventors that the hydrochloride and hydrobromide salts are highly hygroscopic under a condition of 60° C. temperature and 75% relative humidity, resulting in gum type or liquefied form.

Furthermore, it is known that clopidogrel hydrogen sulfate employed in PLAVIX® (Sanofi-Synthelabo Inc.), a marketed tablet composition (see European Patent No. 281,459 B1 and U.S. Pat. No. 6,429,210), is also not sufficiently stable (see H. Agrawal et al, *Talanta*, 61: 581-589, 2003). For example, it was reported PLAVIX® is unstable under an accelerated test condition (40° C., 75% relative humidity, for 3 months), producing significant amounts of impurities (see Y. Gomez et al, *J. Pharm. Biomed. Anal.* 34: 341-348, 2004). In addition, clopidogrel hydrogen sulfate has two polymorphic forms which differ from each other in terms of physicochemical properties, and one of the two forms can be contaminated into the other during its manufacture varying from batch to batch. This makes it difficult to maintain a pharmaceutically required homogeneous polymorphic state.

Accordingly, there has been a need for the better salt of clopidogrel. The inventors have unexpectedly found that crystalline naphthalenesulfonate of clopidogrel is optically pure, less hygroscopic, and more stable toward moisture and heat than conventional acid addition salts. Thus, a pharmaceutical composition comprising same is effective for the prevention or treatment of platelet-associated vascular diseases.

SUMMARY OF THE INVENTION

It is an object of the present invention to provide a crystalline clopidogrel naphthalenesulfonate or a hydrate thereof, and a method for preparing same.

It is another object of the present invention to provide a pharmaceutical composition containing the crystalline clopidogrel naphthalenesulfonate or the hydrate thereof, for the prevention or treatment of platelet-associated vascular disease.

BRIEF DESCRIPTION OF THE DRAWINGS

The above and other objects and features of the present invention will become apparent from the following description of the invention, when taken in conjunction with the accompanying drawings which respectively show.

DETAILED DESCRIPTION OF THE INVENTION

In accordance with one aspect of the present invention, there is provided a crystalline clopidogrel naphthalenesulfonate of formula (I) or a hydrate thereof:

(I)

wherein X is naphthalenemonosulfonate when n is 1 or naphthalenedisulfonate when n is 2.

Further, there is provided a method for preparing a crystalline clopidogrel naphthalenesulfonate of formula (I) or a hydrate thereof, which comprises: reacting a clopidogrel free base of formula (II)

(II)

with a naphthalenesulfonic acid of formula (V) or a hydrate thereof

$$(H^+)_n X^{n-} \quad \quad (V)$$

in an organic solvent, wherein X is naphthalenemonosulfonate when n is 1 or naphthalenedisulfonate when n is 2.

In accordance with another aspect of the present invention, there is provided a pharmaceutical composition containing the crystalline clopidogrel naphthalenesulfonate or the hydrate thereof, for the prevention or treatment of the platelet-associated vascular disease.

The crystalline clopidogrel naphthalenesulfonate of formula (I) according to the present invention is a novel salt of clopidogrel, which is less hygroscopic, thermostable, and can be prepared in a much more optically pure form than any of the conventional salts.

In a preferred embodiment of the present invention, the naphthalenesulfonate group (X) of the crystalline clopidogrel naphthalenesulfonate of formula (I) or the hydrate thereof is derived from 2-naphthalenesulfonic acid, 3-naphthalenesulfonic acid, 1,2-naphthalenedisulfonic acid, 1,3-naphthalenedisulfonic acid, 1,4-naphthalenedisulfonic acid, 1,5-naphthalenedisulfonic acid, 1,6-naphthalenedisulfonic acid, 1,7-naphthalenedisulfonic acid, 1,8-naphthalenedisulfonic acid, 2,3-naphthalenedisulfonic acid, 2,6-naphthalenedisulfonic acid or 2,7-naphthalenedisulfonic acid; and clopidogrel 2-naphthalenesulfonate of formula (Ia) (napsilate according to INN), clopidogrel 1,5-naphthalenedisulfonate of formula (Ib) (napadisilate according to INN) being most preferred.

In the present invention, the clopidogrel naphthalenesulfonate of formula (I) forms a crystalline structure as an anhydrous or hydrous form thereof.

Figure 1:
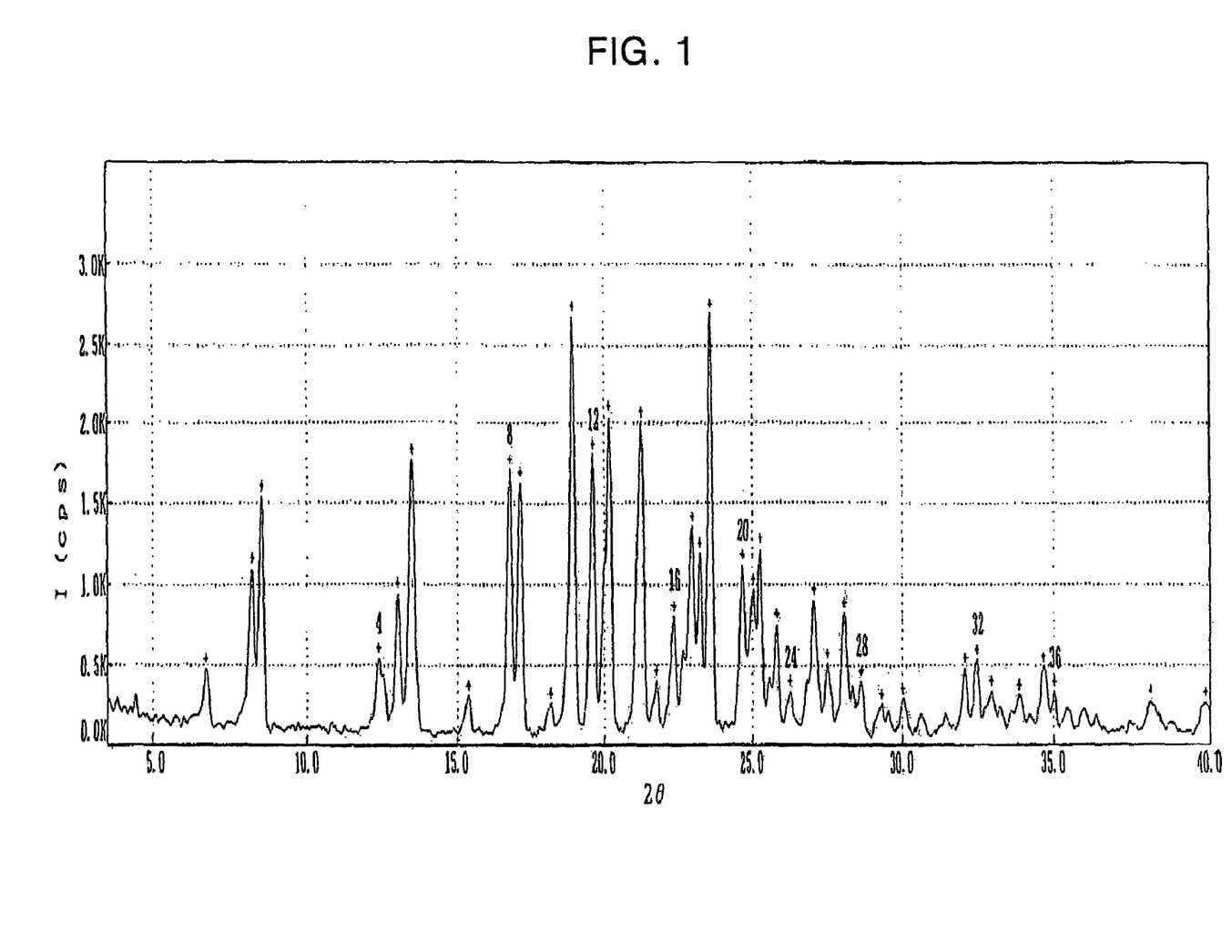
FIG. 1: a powder X-ray diffraction spectrum of the inventive clopidogrel 2-naphthalenesulfonate.
Figure 2:
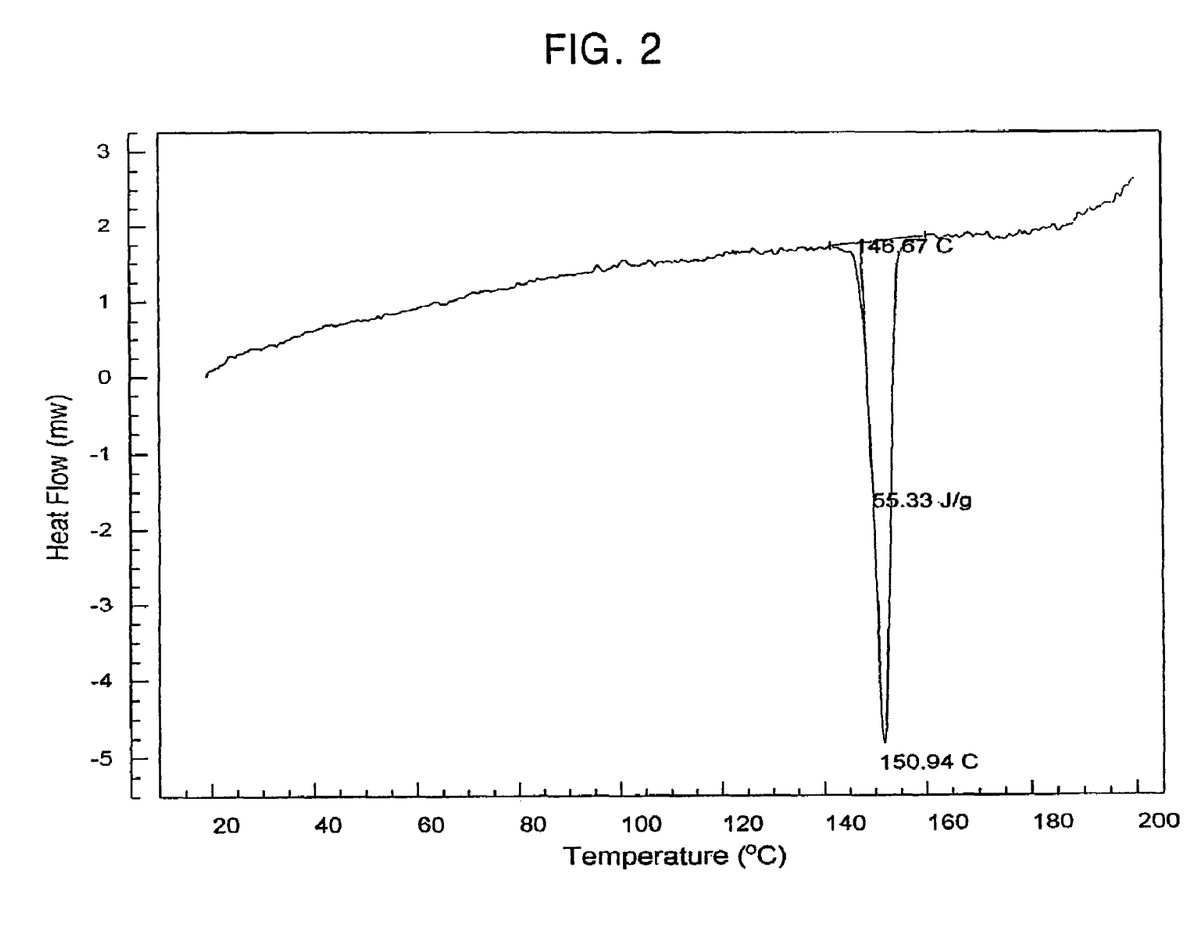
FIG. 2: a differential scanning calorimeter of the inventive clopidogrel 2-naphthalenesulfonate.

For example, the clopidogrel naphthalenesulfonate of formula (Ia) can be crystallized in the anhydrous form whose powder X-ray diffraction (XRD) scan shows major peaks having $I/I_0$ values greater than 10% ($100 \times I/I_0 > 10$) at 2theta ($2\theta$) of 6.7, 8.2, 8.5, 12.4, 13.0, 13.5, 16.8, 17.2, 18.9, 19.6, 20.2, 21.2, 22.3, 22.9, 23.2, 23.6, 24.7, 25.0, 25.3, 25.8, 27.0, 27.5, 28.0, 28.6, 32.1, 32.5, and 34.7 (FIG. 1). Differential scanning calorimeter (DSC) curve of the clopidogrel 2-naphthalenesulfonate at 10° C./min shows an absorption peak of about 55.3 J/g whose heat absorption is started at about 146.7° C. and maximized at about 150.9° C. (FIG. 2). The actually observed melting point of clopidogrel 2-naphthalenesulfonate is 150 to 151° C.

Figure 3:
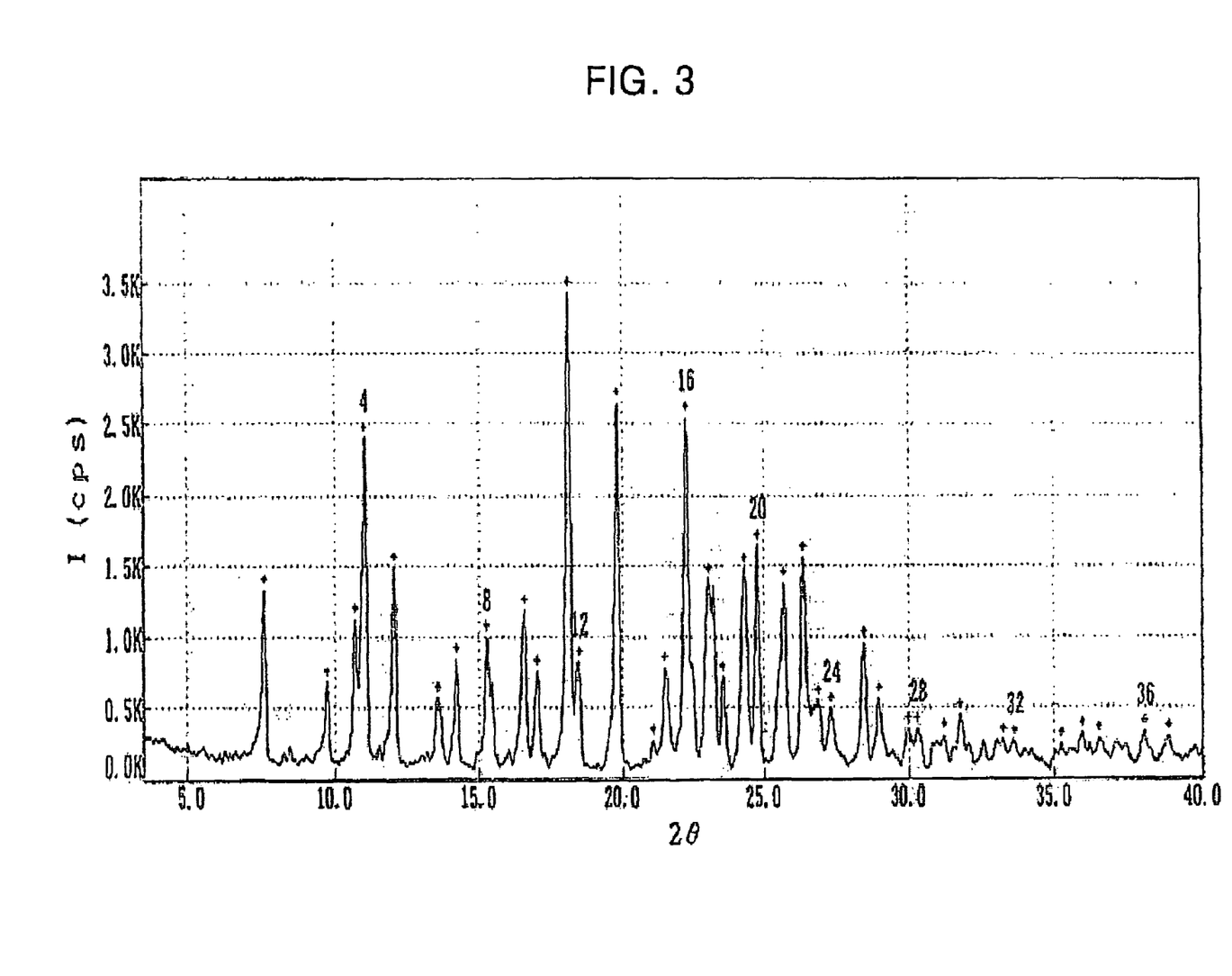
FIG. 3: a powder X-ray diffraction spectrum of the inventive clopidogrel 1,5-naphthalenedisulfonate monohydrate.
Figure 4:
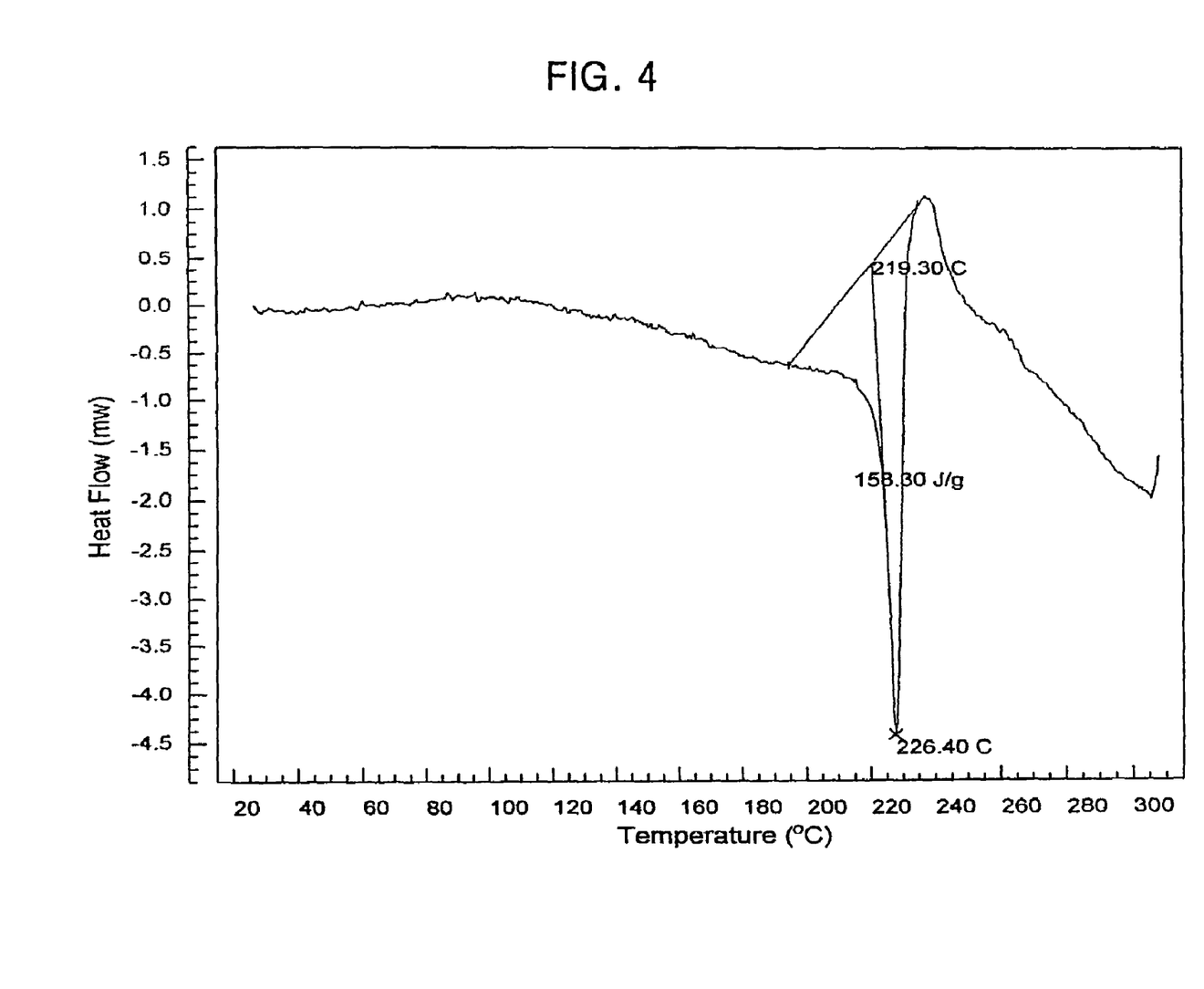
FIG. 4: a differential scanning calorimeter of the inventive clopidogrel 1,5-naphthalenedisulfonate monohydrate.
Figure 5:
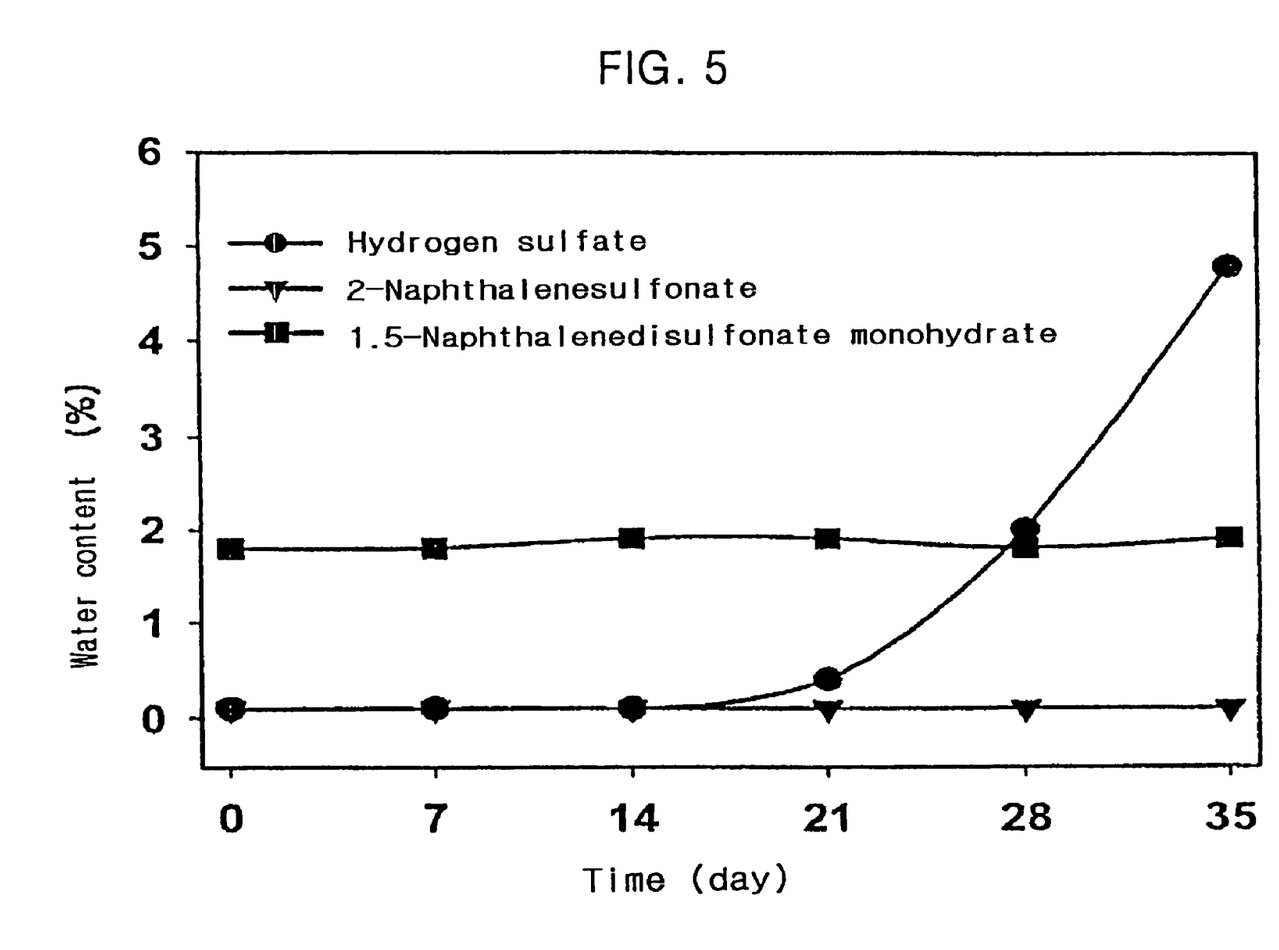
FIG. 5: the time-dependent changes (%) in the water content of the inventive acid addition salt of clopidogrel as compared with clopidogrel hydrogen sulfate.
Figure 6:
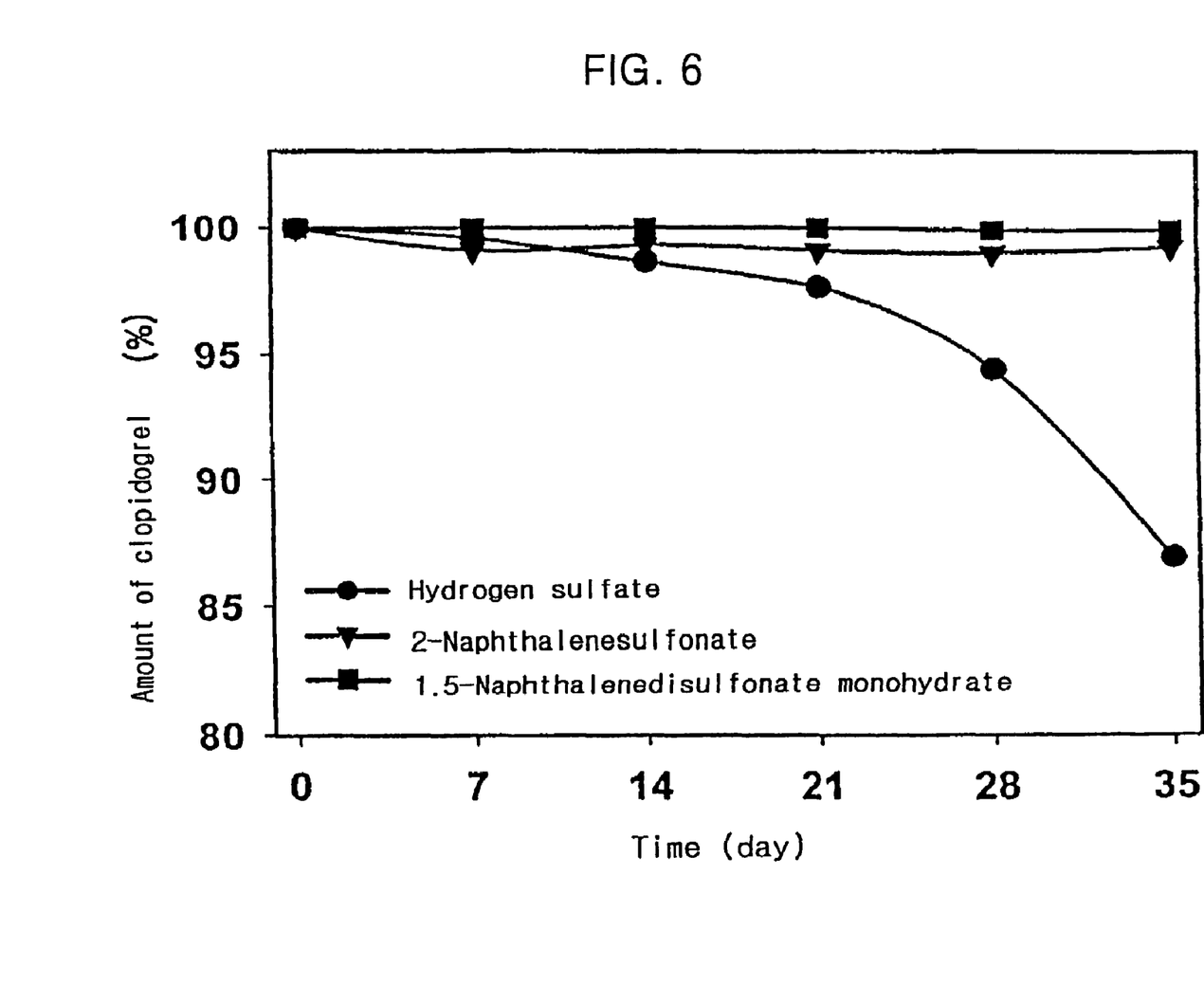
FIG. 6: the time-dependent changes (%) in the amount of clopidogrel of the inventive acid addition salt of clopidogrel as compared with clopidogrel hydrogen sulfate.
Figure 7:
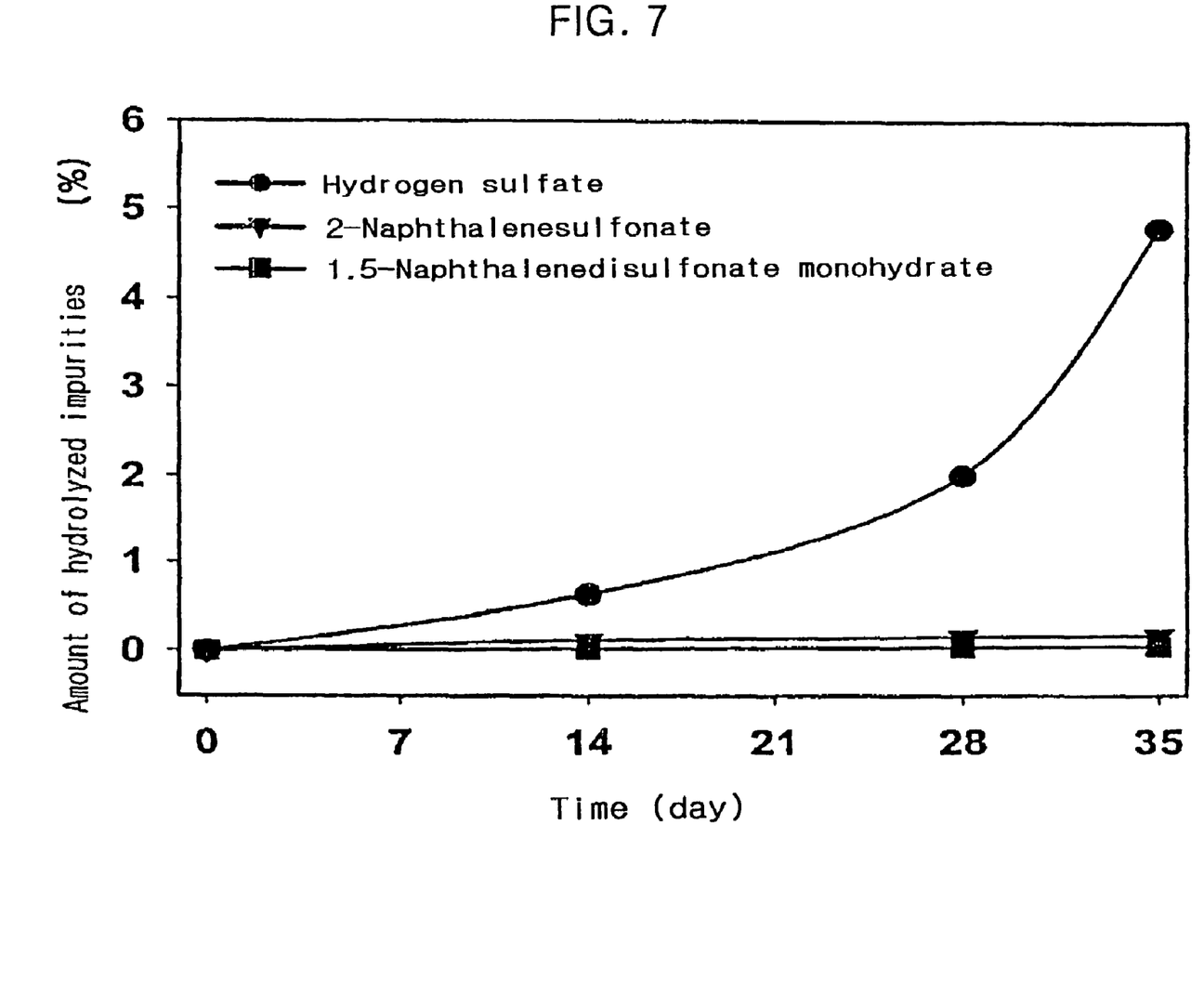
FIG. 7: the time-dependent changes (%) in the amount of hydrolyzed impurities of the inventive acid addition salt of clopidogrel as compared with clopidogrel hydrogen sulfate.
Figure 8:
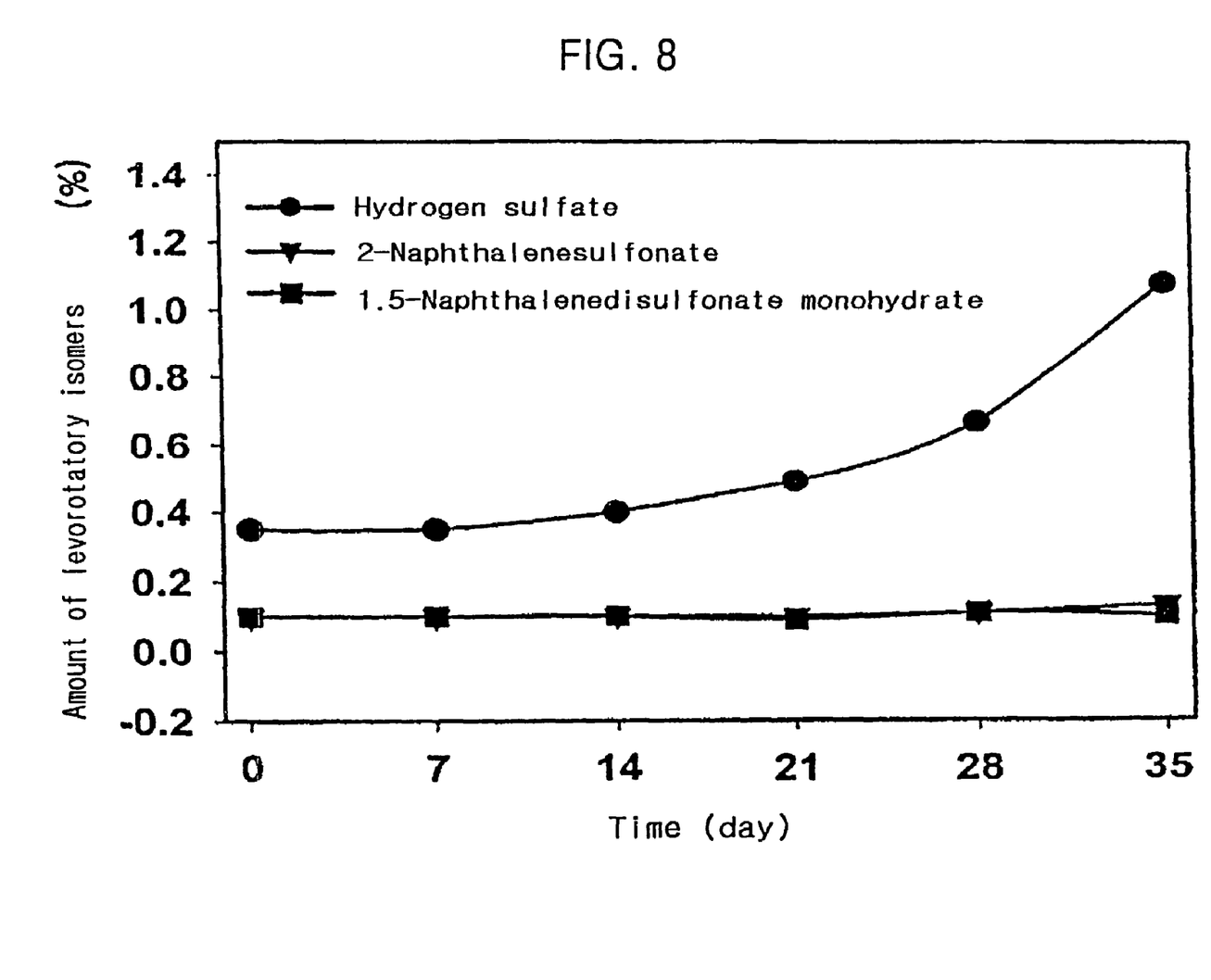
FIG. 8: the time-dependent changes (%) in the amount of levorotatory isomers of the inventive acid addition salt of clopidogrel as compared with clopidogrel hydrogen sulfate.

The clopidogrel 1,5-naphthalenedisulfonate of formula (Ib) crystallizes as a monohydrate whose powder XRD scan shows major peaks having $I/I_0$ values greater than 10% ($100 \times I/I_0 > 10$) at $2\theta$ of 7.6, 9.7, 10.7, 11.0, 12.1, 13.6, 14.2, 15.3, 16.6, 17.0, 18.1, 18.5, 19.8, 21.5, 22.2, 23.0, 23.5, 24.3, 24.8, 25.7, 26.4, 26.9, 27.3, 28.4, and 29.0 (FIG. 3). DSC curve of such clopidogrel 1,5-naphthalenedisulfonate at 5° C./min shows an absorption peak of about 158.3 J/g whose heat absorption is started at about 219.3° C. and maximized about 226.4° C. (FIG. 4). The actually observed melting point of clopidogrel 1,5-naphthalenedisulfonate is 223 to 225° C.

In accordance with the present invention, the clopidogrel naphthalenesulfonate of formula (I) may be prepared by reacting clopidogrel free base with naphthalenemonosulfonic acid, naphthalenedisulfonic acid or a hydrate thereof in an organic solvent.

Specifically, the clopidogrel naphthalenesulfonate of formula (I) is prepared by reacting clopidogrel free base of formula (II) with naphthalenesulfonic acid of formula (V) or a hydrate thereof in an organic solvent having no adverse effect on the salt formation, to obtain a crystalline product, followed by isolating the crystalline product.

The organic solvent which may be used in the present invention includes at least one solvent selected from the group consisting of methyl acetate, ethyl acetate, n-propyl acetate, isopropyl acetate, acetone, methyl ethyl ketone, methyl isobutyl ketone, acetonitrile, methanol, tetrahydrofuran, 1,4- dioxane and a mixture thereof; ethyl acetate, acetone and methanol being most preferred.

In a preferred embodiment of the present invention, the organic solvent may contain water up to 15 v/v %. In the present invention, the organic solvent may be employed in an amount ranging from 1 to 20 by ml volume, preferably 3 to 10 by ml volume, based on 1g weight of the clopidogrel free base. Further, naphthalenesulfonic acid or a hydrate thereof may be employed in an amount ranging from 1.0 to 1.2 moles based on 1.0 mole of the clopidogrel free base.

In the present invention, the reaction may be performed at a temperature ranging from −10° C. to the boiling point of the solvent. However, the reaction is preferably performed at a temperature ranging from 15 to 45° C. for a period ranging from 1 to 24 hours after the addition of naphthalenesulfonic acid or a hydrate thereof to the mixture, followed by cooling and stirring the mixture at a temperature ranging from −10 to 10° C. for a period ranging from 1 to 24 hours after precipitation formation. The precipitates thus formed may be filtered under a reduced pressure, and washed with a suitable solvent. The precipitates are dried using an inert gas such as air and nitrogen under an atmospheric pressure or under a reduced pressure at a temperature ranging from 40 to 70° C.

The clopidogrel free base of formula (II) used as a starting material in the present invention may be prepared according to the known method disclosed in International Patent Publication No. WO 02/59128. As naphthalenesulfonic acid is nontoxic (for example, $LD_{50}$ of 2-naphthalenesulfonic acid is 4,440 mg/kg and sodium salt thereof is 13,900 mg/kg; and that of 1,5-naphthalenedisulfonic acid is 2,420 mg/kg, when they are orally administered to rat; see GISAAA, 39(1), 101, 1974), it can be safely employed in the preparation of acid addition salts for a drug (see S. M. Berge et al, J. Pharm. Sci. 66: 1, 1977).

The crystalline clopidogrel naphthalenesulfonate of formula (I) prepared by the above method is non-hygroscopic, stable against moisture and heat, and optically pure. Thus, it can be useful for the prevention or treatment of the platelet-associated vascular disease selected from the group consisting of stroke, cerebral arteriosclerosis, myocardial infarction, angina pectoris, arrhythmia, peripheral arteries disease, and Burger's disease.

In a preferred embodiment, a pharmaceutical composition comprising the inventive clopidogrel naphthalenesulfonate as an active ingredient may be administered via the oral route, and, thus, the pharmaceutical composition of the present invention may be in the form of solutions, suspensions, tablets, pills, capsules, powders, and the like.

The pharmaceutical composition according to the present invention may be formulated together with pharmaceutically acceptable carriers, diluents, or excipients, if necessary.

Examples of suitable carriers, diluents, or excipients are excipients such as starch, sugar and mannitol; filling agents or increasing agents such as calcium phosphate and silica derivatives; binding agents such as cellulose derivatives of carboxymethylcellulose or hydroxypropylcellulose, gelatin, arginic acid salt, and polyvinylpyrrolidone; lubricating agents such as talc, magnesium or calcium stearate, hydrogenated castor oil and solid polyethylene glycol; disintegrants such as povidone, croscarmellose sodium, and crospovidone; and surfactants such as polysorbate, cetyl alcohol and glycerol monostearate. Further, various pharmaceutical composition comprising a specific amount of active ingredient, together with or without additives such as said excipients, diluents or additives, may be prepared in accordance with any of the conventional procedures (see Remington's Pharmaceutical Science, Mack Publishing Company, Easton, Pa., 19$^{th}$ Edition, 1995).

In a preferred embodiment, the pharmaceutical composition according to the present invention may contain the clopidogrel naphthalenesulfonate or the hydrate thereof in an amount ranging from 0.1 to 95% by weight, preferably 1 to 70% by weight based on the total composition weight.

The clopidogrel naphthalenesulfonate of formula (I) according to the present invention may be orally administered to a subject in a dose ranging from 1 to 1000 mg/60 kg weight, preferably 25 to 250 mg/60 kg weight per day.

The present invention will be described in further detail with reference to Examples. However, it should be understood that the present invention is not restricted by the specific Examples.

The analysis conditions of HPLC employed in Examples are listed below.

Condition A: For the measurement of an assay of an acid addition salt of clopidogrel
  Column: Kromasil C18, 5 µm (250 mm×4.6 mm)
  Detector: 220 nm
  Flow rate: 1.5 ml/minute
  Mobile phase: $Na_2HPO_4$—$NaH_2PO_4$ buffer solution: THF: $CH_3CN$=5:2:3 (v/v)

Condition B: For the measurement of an amount of hydrolyzed impurities of an acid addition salt of clopidogrel
  Column: Capcellpak C18 MG, 5 µm (250 mm×4.6 mm)
  Detector: 210 nm
  Flow rate: 1.0 ml/min.
  Mobile phase: $KH_2PO_4$ buffer solution/$CH_3CN$ (70/30): $KH_2PO_4$ buffer solution/$CH_3CN$ (30/70)=0:100 100:0 (v/v, gradient elution)

Condition C: For the measurement of an optical purity of an acid addition salt of clopidogrel
  Column: Chiralpak AD, 5 µm (250 mm×4.6 mm)
  Detector: 210 nm
  Flow rate: 1.0 ml/min.
  Mobile phase: n-hexane: isopropanol=90:10 (v/v)

COMPARATIVE EXAMPLE 1

Preparation of Clopidogrel Hydrogen Sulfate

Clopidogrel hydrogen sulfate as a crystalline form 2 was prepared according to the method disclosed in U.S. Pat. No. 6,429,210 from clopidogrel free base having an optical purity of 99.3% ee which had been prepared by the method disclosed in International Patent Publication No. WO 02/59128.

m.p.: 176~177° C.; water (Karl-Fisher titrator): below 0.1%; assay (HPLC, condition A): 99.94%; and optical purity (HPLC, condition C): 99.3% ee

EXAMPLE 1

Preparation of Clopidogrel 2-naphthalenesulfonate (Clopidogrel Napsilate; Formula (Ia))

50 g of clopidogrel free base having an optical purity of 99.3% ee which was prepared by the method similar to that disclosed in International Patent Publication No. WO 02/59128 was dissolved in 100 ml of ethyl acetate, and a solution containing 34.8 g of 2-naphthalenesulfonic acid monohydrate dissolved in a mixture of 150 ml of ethyl acetate and 5 ml of water was added thereto dropwise over a period of 30 minutes. Then, the mixture was stirred at room temperature for 12 hours, and then, at a temperature ranging from 0 to 5 for 4 hours. The precipitates formed were filtered, washed with 30 ml of ethyl acetate and dried at 50° C., to obtain 71.6 g of the title compound (yield: 87%) as an white crystal.

m.p.: 151° C.; water (Karl-Fisher titrator): below 0.1%; aaasy (HPLC, condition A): 99.95%; optical purity (HPLC, condition C): 99.8% ee; and elemental analysis for $C_{16}H_{16}ClNO_2S$ $C_{10}H_8O_3S$ (%): Calculated, C, 58.91; H, 4.56; N, 2.64, S 12.10; Found, C 58.77, H 4.61, N 2.60, S 12.27

$^1$H-NMR (300 MHz, DMSO-d$^6$, ppm): δ 3.08 (brs, 2H), 3.50 (brs, 2H), 3.74 (s, 3H), 4.25 (brs, 2H), 5.68 (s, 1H), 6.88 (d, 1H, J=4.9 Hz), 7.44 (d, 1H, J=4.9 Hz), 7.53~7.60 (m, 4H), 7.62~7.77 (m, 3H), 7.80~7.98 (m, 3H), 8.15 (s, 1H), 10.85 (brs, 1H)

IR (KBr, cm$^{-1}$): 3475, 2967, 1749, 1475, 1438, 1326, 1220, 1165, 1090, 1031 DSC (10° C./minute): starting point 146.67° C., lowest point 150.94° C. (heat absorption 55.33 J/g)

The result of powder X-ray diffraction analysis for the crystalline state of the clopidogrel 2-naphthalenesulfonate showed that the clopidogrel 2-naphthalenesulfonate was crystal having the characteristic diffraction pattern as shown in FIG. 1. The main diffraction peaks having I/I$_0$ value greater than 10%, are listed in Table 1.

TABLE 1

| 2θ(±2) | d | I/I$_0$ (%) |
|---|---|---|
| 6.7 | 13.2 | 13.5 |
| 8.2 | 10.8 | 38.1 |
| 8.5 | 10.4 | 55.7 |
| 12.4 | 7.2 | 17.6 |
| 13.0 | 6.8 | 32.8 |
| 13.5 | 6.6 | 65.2 |
| 16.8 | 5.3 | 63.7 |
| 17.2 | 5.2 | 60.2 |
| 18.9 | 4.7 | 100.0 |
| 19.6 | 4.5 | 66.0 |
| 20.2 | 4.4 | 75.7 |
| 21.2 | 4.2 | 73.3 |
| 22.3 | 4.0 | 25.1 |
| 22.9 | 3.9 | 46.4 |
| 23.2 | 3.8 | 40.8 |
| 23.6 | 3.8 | 99.8 |
| 24.7 | 3.6 | 38.3 |
| 25.0 | 3.6 | 32.7 |
| 25.3 | 3.5 | 42.2 |
| 25.8 | 3.5 | 24.3 |
| 27.0 | 3.3 | 30.3 |
| 27.5 | 3.2 | 15.1 |
| 28.0 | 3.2 | 27.3 |
| 28.6 | 3.1 | 11.4 |
| 32.1 | 2.8 | 14.9 |
| 32.5 | 2.8 | 16.4 |
| 34.7 | 2.6 | 14.4 |

2θ: angle of diffraction, d: distance within each crystal face,
I/I$_0$ (%): relative intensity of peak

EXAMPLE 2

Preparation of Clopidogrel 1,5-naphthalenedisulfonate Monohydrate (Clopidogrel Napadisilate; Formula (Ib))

50 g of clopidogrel free base having an optical purity of 99.3% ee prepared by the method similar to that disclosed in International Patent Publication No. WO 02/59128 was dissolved in 300 ml of acetone, and a solution containing 28.9 g of 1,5-naphthalenedisulfonic acid tetrahydrate dissolved in a mixture of 290 ml of acetone and 10 ml of water was added thereto dropwise over a period of 30 minutes. Then, the mixture was stirred at room temperature for 12 hours, and then, at a temperature ranging from 0 to 5° C. for 4 hours. The precipitates thus formed were filtered, washed with 100 ml of cold acetone and dried at 50° C., to obtain 66.7 g of the title compound (yield: 90%) as an white crystal.

m.p.: 223~225° C.; water (Karl-Fisher detector): 1.95% (monohydrate theoretical value: 1.90%; assay (HPLC, condition A): 99.96%; optical purity (HPLC, condition C): 99.8% ee; and elemental analysis for $(C_{16}H_{16}ClNO_2S)_2$ $C_{10}H_8O_6S_2H_2O$ (%): Calculated, C 53.10, H 4.46, N 2.95, S 13.50; Found, 53.04, H 4.52, N 2.91, S 13.49

$^1$H-NMR (300 MHz, DMSO-d$^6$, ppm): δ 3.08 (brs, 2H), 3.47 (brs, 2H), 3.76 (s, 3H), 4.23 (brs, 2H), 5.66 (s, 1H), 6.89 (d, 1H, J=5.0 Hz), 7.33~7.74 (m, 6H), 7.93 (d, 1H, J=7.0 Hz), 8.88 (d, 1H, J=8.5 Hz)

IR (KBr, cm$^{-1}$): 3648, 3462, 2956, 1745, 1436, 1338, 1243, 1225, 1155, 1026 DSC (5° C./minute): starting point 219.3° C., lowest point 226.4° C. (heat absorption 158.3 J/g)

The result of powder X-ray diffraction analysis for the crystalline state of the clopidogrel 1,5-naphthalenedisulfonate monohydrate showed that clopidogrel 1,5-naphthalenedisulfonate monohydrate was crystal having the characteristic diffraction peaks as shown in FIG. 3. The diffraction peaks having I/I$_0$ value greater than 10% are listed in Table 2.

TABLE 2

| 2θ(±2) | d | I/I$_0$ (%) |
|---|---|---|
| 7.6 | 11.6 | 35.9 |
| 9.7 | 9.1 | 17.2 |
| 10.7 | 8.3 | 30.4 |
| 11.0 | 8.0 | 68.7 |
| 12.1 | 7.3 | 41.6 |
| 13.6 | 6.5 | 14.3 |
| 14.2 | 6.2 | 22.4 |
| 15.3 | 5.8 | 26.9 |
| 16.6 | 5.3 | 32.0 |
| 17.0 | 5.2 | 19.3 |
| 18.1 | 4.9 | 100.0 |
| 18.5 | 4.8 | 22.0 |
| 19.8 | 4.5 | 76.7 |
| 21.5 | 4.1 | 19.7 |
| 22.2 | 4.0 | 72.0 |
| 23.0 | 3.9 | 37.9 |
| 23.5 | 3.8 | 17.6 |
| 24.3 | 3.7 | 40.5 |
| 24.8 | 3.6 | 45.8 |
| 25.7 | 3.5 | 37.4 |
| 26.4 | 3.4 | 42.7 |
| 26.9 | 3.3 | 12.5 |
| 27.3 | 3.3 | 10.9 |
| 28.4 | 3.1 | 24.9 |
| 29.0 | 3.1 | 13.2 |

2θ: angle of diffraction, d: distance within each crystal face,
I/I$_0$ (%): relative intensity of peak

EXAMPLE 3

Stability Test of Acid Addition Salts of Clopidogrel Under Moist and Heated Condition The clopidogrel hydrogen sulfate obtained in Comparative Example 1, and the clopidogrel 2-naphthalenesulfonate and the clopidogrel 1,5-naphthalenedisulfonate monohydrate obtained in Examples 1 and 2, respectively, were subjected to a condition of 60±2° C. and 75±5% relative humidity for a period of over 30 days to test their stabilities. Specifically, the ratios of the remaining amounts of the active compound at 7, 14, 21, 28, and 35 day relative to that of the initial day (0) were measured using HPLC. The assay of the acid addition salt of clopidogrel was measured using HPLC condition A, the amount of hydrolyzed impurities of the acid addition salt of clopidogrel was measured using HPLC condition B, the optical purity of the acid addition salt of clopidogrel (i.e., the amount of the levorotatory isomers) was measured using the HPLC condition C, and the water content of the acid addition salt of clopidogrel was measured with a Karl-Fisher titrator. The results are shown in Tables 3 to 6 and FIGS. 5 to 8, respectively.

TABLE 3

Comparison of hygroscopicity of an acid addition salt of clopidogrel

| Acid addition salt of clopidogrel | Water content (%) | | | | | |
|---|---|---|---|---|---|---|
| | 0 day | 7 days | 14 days | 21 days | 28 days | 35 days |
| Hydrogen sulfate | 0.1 | 0.1 | 0.1 | 0.4 | 2.0 | 4.8 |
| 2-Naphthalenesulfonate | 0.1 | 0.1 | 0.1 | 0.1 | 0.1 | 0.1 |
| 1,5-Naphthalenedisulfonate monohydrate | 1.8 | 1.8 | 1.9 | 1.9 | 1.8 | 1.9 |

TABLE 4

Comparison of amount of an acid addition salt of clopidogrel

| Acid addition salt of clopidogrel | Relative amount compared to the initial amount (%) | | | | | |
|---|---|---|---|---|---|---|
| | 0 day | 7 days | 14 days | 21 days | 28 days | 35 days |
| Hydrogen sulfate | 100 | 99.6 | 98.7 | 97.7 | 94.4 | 87.0 |
| 2-Naphthalenesulfonate | 100 | 99.1 | 99.3 | 99.1 | 99.0 | 99.2 |
| 1,5-Naphthalenedisulfonate monohydrate | 100 | 100 | 100 | 100 | 99.9 | 99.9 |

TABLE 5

Comparison of hydrolyzed impurities (formula (III)) of an acid addition salt of clopidogrel

| Acid addition salt of clopidogrel | Amount of hydrolyzed impurities of an acid addition salt of clopidogrel (%) | | | |
|---|---|---|---|---|
| | 0 day | 14 days | 28 days | 35 days |
| Hydrogen sulfate | 0.0 | 0.63 | 2.0 | 4.8 |
| 2-Naphthalenesulfonate | 0.0 | 0.12 | 0.16 | 0.18 |
| 1,5-Naphthalenedisulfonate monohydrate | 0.0 | 0.02 | 0.04 | 0.05 |

TABLE 6

Comparison of levorotatory isomers (formula (IV)) of an acid addition salt of clopidogrel

| Acid addition salt of clopidogrel | Amount of levorotatory isomers of an acid addition salt of clopidogrel (%) | | | | | |
|---|---|---|---|---|---|---|
| | 0 day | 7 days | 14 days | 21 days | 28 days | 35 days |
| Hydrogen sulfate | 0.35 | 0.35 | 0.40 | 0.49 | 0.67 | 1.08 |
| 2-Naphthalenesulfonate | 0.10 | 0.10 | 0.10 | 0.10 | 0.11 | 0.13 |
| 1,5-Naphthalenedisulfonate monohydrate | 0.10 | 0.10 | 0.10 | 0.09 | 0.11 | 0.10 |

As shown in Tables 3 to 6, the inventive clopidogrel naphthalenesulfonate is less hygroscopic, and more stable against moisture and heat. Thus, there was no significant decline in the amount of optically pure clopidogrel after storage under a severe condition for a long period, and hydrolyzed impurities of the clopidogrel naphthalenesulfonate were far less in amount than that observed for hydrogen sulfate. These results confirm that a pharmaceutical composition comprising the inventive clopidogrel naphthalenesulfonate according to the present invention is more effective than conventional acid addition salts in the prevention or treatment for the platelet-associated vascular disease.

EXAMPLE 4

Effect of Increasing Optical Purity During Clopidogrel Salt Formation

Clopidogrel free bases having optical purities of about 90% ee, 95% ee and 98% ee, respectively, were prepared, and, clopidogrel hydrogen sulfates, and clopidogrel 2-naphthalenesulfonates and clopidogrel 1,5-naphthalenedisulfonate monohydrates thereof were prepared using the procedures described in Comparative Example 1, and Examples 1 and 2, respectively. The optical purities of the acid addition salts then obtained were measured under HPLC condition C, and the extents of optical purity improvement are shown in Table 7.

TABLE 7

| Starting material | Obtained acid addition salt of clopidogrel | | |
|---|---|---|---|
| Clopidogrel free base | Hydrogen sulfate | 2-Naphthalenesulfonate | 1,5-Naphthalenedisulfonate monohydrate |
| 90.0 | 89.4 | 98.3 | 97.4 |
| 94.9 | 94.7 | 98.8 | 98.7 |
| 97.7 | 97.7 | 99.5 | 99.4 |

Unit: % ee (the excess amount of enantiomers)

As shown in Table 7, the optical purity of the clopidogrel naphthalenesulfonate according to the present invention was markedly enhanced during the process of preparing same, while that of clopidogrel hydrogen sulfate was not improved.

Clopidogrel is liable to be partially racemized to its levorotatory isomer, and thus, a plurality of purification steps is required to achieve a pharmaceutically acceptable optical purity. However, the inventive method of preparing the naphthalenesulfonate provides a product which meets the pharmaceutical optical purity requirements, so that separate optical purification steps can be omitted.

TEST EXAMPLE 1

Inhibitory Effect of Clopidogrel Naphthalenesulfonate Against Platelet Aggregation The pharmacological activities for preventing platelet aggregation of the clopidogrel hydrogen sulfate obtained in Comparative Example 1, and the inventive clopidogrel 2-naphthalenesulfonate and clopidogrel 1,5-naphthalenedisulfonate monohydrate obtained in Examples 1 and 2, respectively, were tested using rat blood in accordance with the standard method (see Born G.V.R & Cross, *J. Physiol.* 168: 178-195, 1963; 0. Takahashi, *Food & Chemical Toxicology* 38: 203-218, 2000). The platelet aggregation inhibition test was performed ex vivo, and the inhibitory activities of the acid addition salts against platelets aggregation induced by adenosine-diphosphate (ADP), collagen and thrombin, respectively, were measured.

Twenty 11 to 12-weeks old female Sprague-Dawley rats (average weight: 270±25 g) were divided into four groups each consisting of five rats, and each group of rats was orally administered with 20.0 mg/kg of clopidogrel hydrogen sulfate (15.3 mg/kg as clopidogrel), 25.2 mg/kg of clopidogrel 2-naphthalenesulfonate, and 22.6 mg/kg of clopidogrel 1,5-naphthalenedisulfonate monohydrate dissolved in 1% DMSO based on a volume of 10 ml/kg body weight. For the control group of rats, only 1% DMSO solution was administered.

Blood samples were taken using a syringe pre-charged with 3.8% citric acid solution from the abdominal artery of the animals under anesthesia, and the blood samples were centrifuged at 4° C. and 1,000 rpm for 10 minutes to separate platelet-rich plasma (PRP). The separated plasma was further centrifuged four times at 4° C. and 1,000 rpm to obtain PRP for test. A portion of PRP was further centrifuged at 4° C. and 3,000 rpm for 10 minutes to prepare precipitated platelet, and the precipitated platelet was washed with a buffer (138 mM NaCl, 2.7 mM KCl, 12 mM NaHCO$_3$, 0.36 mM NaH$_2$PO$_4$, 5.5 mM glucose, 1 mM EDTA: pH 6.5). Then, the platelet was suspended in a buffer (138 mM NaCl, 2.7 mM KCl, 12 mM NaHCO$_3$, 0.36 mM NaH$_2$PO$_4$, 0.49 mM MgCl$_2$, 0.25% gelatin, 5.5 mM glucose: pH 7.4) such that the optical density (OD) value at 260 nm corresponded to a number of platelet which is about 1×10$^8$.

To induce platelet aggregation, ADP standard solution was added to the above PRP to determine the concentration until the final concentration of the ADP became 5 µM. Further, a collagen standard solution (final concentration 5 µg/ml) and thrombin standard solution (final concentration 0.1 U/ml) was added to the above washing platelet solution to induce platelet aggregation. Each of the samples was stirred at 37° C. and 900 rpm to measure the amount of platelet aggregation using a aggregometer (Chrono-log Platelet Aggregometer). The degrees of platelet aggregation and inhibition were calculated using formulae 1 and 2, and the results are shown in Table 8.

Degree of aggregation (%)=[(measured aggregation height)/(aggregation height when 100% was aggregated)]×100  <Formula 1>

Degree of inhibition (%)=[(aggregation height of control group)−(aggregation height of drug administration group)]/(aggregation height of control group)×100  <Formula 2>

TABLE 8

The inhibitory effect of acid addition salts of clopidogrel

| | Aggregation inducing material and concentration | | | | | |
|---|---|---|---|---|---|---|
| | ADP (5 µM) | | Collagen (5 µg/ml) | | Thrombin (0.1 U/ml) | |
| Administered Drug | Aggregation ratio (%)* | Inhibition ratio (%) | Aggregation ratio (%)* | Inhibition ratio (%) | Aggregation ratio (%)* | Inhibition ratio (%) |
| Control | 35.88 ± 2.43 | — | 80.31 ± 2.80 | — | 82.78 ± 2.11 | — |
| Hydrogen sulfate | 5.00 ± 0.60 | 86.1 | 12.19 ± 1.70 | 84.8 | 27.22 ± 1.52 | 67.1 |
| 2-Naphthalenesulfonate | 2.94 ± 0.21 | 91.8 | 1.88 ± 0.25 | 97.9 | 15.00 ± 1.71 | 81.9 |
| 1,5-Naphthalenedisulfonate monohydrate | 4.12 ± 0.14 | 88.5 | 3.75 ± 0.40 | 95.3 | 23.61 ± 1.43 | 71.5 |

*p < 0.001
**amounts of 2-naphthalenesulfonate and 1,5-naphthalenedisulfonate monohydrate corresponding to the amount of 20 mg of hydrogen sulfate are 25.2 mg and 22.6 mg, respectively, which corresponds to clopidogrel 15.3 mg.

TEST EXAMPLE 2

Effect of Clopidogrel Naphthalenesulfonate on Bleeding Time

Effects on the bleeding time of the conventional clopidogrel hydrogen sulfate obtained in Comparative Example 1 and the inventive clopidogrel 2-naphthalenesulfonate and clopidogrel 1,5-naphthalenedisulfonate monohydrate obtained in Examples 1 and 2, respectively, were tested using rat in accordance with the standard method (see Dejana E & Villa S, *Thromb. Haemostas.* 48: 108-111, 1982). The bleeding time is an index representing the extent of thrombus formed by platelet aggregation and tests were performed using male and female rats.

Forty 11 to 12-weeks old male and female Sprague-Dawley rats (average weight: 270±25 g) were divided into four groups each consisting of five male rats and five female rats, and the male rats of the first group were each orally administered with 5.0 mg/kg of clopidogrel hydrogen sulfate (3.83 mg/kg as clopidogrel) and the female rats of the first group were each orally administered with 2.5 mg/kg (1.92 mg/kg as clopidogrel). For the second group, the male and female rats were orally each administered with 6.30 mg/kg and 3.15 mg/kg of clopidogrel 2-naphthalenesulfonate, respectively, and for the third group, the male and female rats were each orally administered with 5.65 mg/kg and 2.83 mg/kg of clopidogrel 1,5-naphthalenedisulfonate monohydrate, respectively. The drug was orally administered in the form of 1% DMSO solution in an amount in volume of 10 ml/kg body weight. As a comparison, only 1% DMSO solution was administered to the last group of rats.

After fixing an unanesthetized rat with an experimental holder, the tail of the rat was pierced at a position of 1.5 cm from the end of tail using a need of 26 G×½, 0.45×13 mm at a depth of 1 mm. The time of bleeding to cease was measured with absorbing the bleeding blood on a filter paper every 10 second. The result is shown in Table 9.

TABLE 9

Effect on bleeding time of an acid addition salt of clopidogrel

| Administered Drug | Female | | Male | |
|---|---|---|---|---|
| | Amount of administered drug (mg/kg) | Bleeding time (sec.)* | Amount of Administered drug (mg/kg) | Bleeding time (sec.)* |
| Comparison | — | 85 ± 7.1 | — | 105 ± 5.0 |
| Hydrogen sulfate | 2.50** | 127.5 ± 10.6 | 5.00*** | 135 ± 8.7 |
| 2-Naphthalenesulfonate | 3.15** | 157 ± 10.6 | 6.30*** | 190 ± 5.0 |
| 1,5-Naphthalenedisulfonate monohydrate | 2.83** | 152.5 ± 3.5 | 5.65*** | 163 ± 5.8 |

*$p < 0.001$
**2.50 mg of hydrogen sulfate, 3.15 mg of 2-naphthalenesulfonate and 2.83 mg of 1,5-naphthalenedisulfonate monohydrate correspond to 1.92 mg of clopidogrel.
***5.00 mg of hydrogen sulfate, 6.30 mg of 2-naphthalenesulfonate and 5.65 mg of 1,5-naphthalenedisulfonate monohydrate correspond to 3.83 mg of clopidogrel.

As can be seen from Tables 8 and 9, the inventive clopidogrel naphthalenesulfonate inhibits the platelet aggregation induced by ADP, collagen or thrombin, and significantly extends the bleeding time as compared with the conventional acid addition salts, e.g., hydrogen sulfate. Therefore, the clopidogrel naphthalenesulfonate according to the present invention is more effective than any of the conventional acid addition salts in the prevention or treatment for platelet-associated vascular diseases.

The clopidogrel naphthalenesulfonate of the present invention may be formulated alone or in a combination with pharmaceutically acceptable additives, according to any of the conventional methods used to prepare soft or hard capsules and tablets.

The following Preparation Examples are intended to further illustrate the present invention without limiting its scope.

PREPARATION EXAMPLE 1

Soft or Hard Capsule 1

A gelatin capsule was prepared using the following ingredients:

| | Quantity(mg/capsule) |
|---|---|
| Clopidogrel 2-naphthalenesulfonate | 120 |
| Lactose | 100 |
| Corn starch | 25 |
| Silicon dioxide colloid | 3 |
| Magnesium stearate | 2 |
| Total | 250 |

PREPARATION EXAMPLE 2

Soft or Hard Capsule 2

A gelatin capsule was prepared using the following ingredients:

| | Quantity(mg/capsule) |
|---|---|
| Clopidogrel 1,5-naphthalenedisulfonate monohydrate | 110 |
| Lactose | 110 |
| Corn starch | 25 |
| Silicon dioxide colloid | 3 |
| Magnesium stearate | 2 |
| Total | 250 |

PREPARATION EXAMPLE 3

Tablet 1

A tablet was prepared using the following ingredients:

|  | Quantity(mg/tablet) |
| --- | --- |
| Clopidogrel 2-naphthalenesulfonate | 120 |
| Anhydrous lactose | 90 |
| Microcrystalline cellulose | 30 |
| Hydroxypropylcellulose | 5 |
| Polysorbate | 2 |
| Hydrogenated castor oil | 1 |
| Magnesium stearate | 1 |
| Solid polyethylene glycol | 1 |
| Total | 250 |

PREPARATION EXAMPLE 4

Tablet 2

A tablet was prepared using the following ingredients:

|  | Quantity(mg/tablet) |
| --- | --- |
| Clopidogrel 1,5-naphthalenedisulfonate monohydrate | 110 |
| Anhydrous lactose | 100 |
| Microcrystalline cellulose | 30 |
| Hydroxypropylcellulose | 5 |
| Polysorbate | 2 |
| Hydrogenated castor oil | 1 |
| Magnesium stearate | 1 |
| Solid polyethylene glycol | 1 |
| Total | 250 |

As discussed above, the clopidogrel naphthalenesulfonate according to the present invention easily meets the optical purity requested by the pharmaceutical formulation simply by carrying out the inventive process. The clopidogrel naphthalenesulfonate is very stable against moisture and heat, so that a high purity of active ingredient can be maintained for a prolonged time. Further, The clopidogrel naphthalenesulfonate is better than the conventional salts in terms of pharmaceutical effects in animal experiments using rats. Accordingly, the clopidogrel naphthalenesulfonate according to the present invention is more useful than any of the conventional acid addition salts in the prevention or treatment for the platelet-associated vascular disease.

While the invention has been described with respect to the above specific embodiments, it should be recognized that various modifications and changes may be made to the invention by those skilled in the art which also fall within the scope of the invention as defined by the appended claims.

What is claimed is:

1. A crystalline monohydrate of clopidogrel 1,5-naphthalenedisulfonate represented by formula (Ib)

(Ib)

2. The crystalline monohydrate of clopidogrel 1,5-naphthalenedisulfonate of claim 1, whose powder X-ray diffraction scan shows major peaks having $I/I_0$ values greater than 10% at $2\theta$=7.6, 9.7, 10.7, 11.0, 12.1, 13.6, 14.2, 15.3, 16.6, 17.0, 18.1, 18.5, 19.8, 21.5, 22.2, 23.0, 23.5, 24.3, 24.8, 25.7, 26.4, 26.9, 27.3, 28.4, 29.0.

3. A method for preparing a crystalline monohydrate of clopidogrel 1,5-naphthalenedisulfonate of formula (Ib), which comprises:

(Ib)

reacting a clopidogrel free base of formula (II)

(II)

with a 1,5-naphthalenedisulfonic acid hydrate, in an organic solvent selected from the group consisting of methyl acetate, ethyl acetate, n-propyl acetate, isopropyl acetate, acetone, methyl ethyl ketone, methyl isobutyl ketone, acetonitrile, methanol, tetrahydrofuran, 1,4-dioxane and a mixture thereof.

4. The method of claim 3, wherein the crystalline monohydrate of clopidogrel 1,5-naphthalenedisulfonate is characterized in the powder X-ray diffraction scan by showing major peaks having $I/I_0$ values greater than 10% at $2\theta$=7.6, 9.7, 10.7, 11.0, 12.1, 13.6, 14.2, 15.3, 16.6, 17.0, 18.1, 18.5, 19.8, 21.5, 22.2, 23.0, 23.5, 24.3, 24.8, 25.7, 26.4, 26.9, 27.3, 28.4, 29.0.

5. The method of claim 3, wherein the 1,5-naphthalenedisulfonic acid hydrate is employed in an amount ranging from 0.5 to 0.6 moles based on 1.0 mole of the clopidogrel free base.

6. A pharmaceutical composition comprising the crystalline monohydrate of clopidogrel 1,5-naphthalenedisulfonate of claim 1 as an active ingredient in the presence of a pharmaceutically acceptable carrier, diluent or excipient.

7. The pharmaceutical composition of claim 6, wherein the crystalline monohydrate of clopidogrel 1,5-naphthalenedisulfonate is present in the amount ranging from 0.1 to 95% by weight based on the total weight of the composition in oral dosage unit.

8. The pharmaceutical composition of claim 6, wherein the crystalline monohydrate of clopidogrel 1,5-naphthalenedisulfonate is present in the amount ranging from 1 to 70% by weight based on the total weight of the composition in oral dosage unit.

9. The pharmaceutical composition of claim 6, wherein the crystalline monohydrate of clopidogrel 1,5-naphthalenedisulfonate is characterized in the powder X-ray diffraction scan by showing major peaks having $I/I_0$ values greater than 10% at $2\theta$=7.6, 9.7, 10.7, 11.0, 12.1, 13.6, 14.2, 15.3, 16.6, 17.0, 18.1, 18.5, 19.8, 21.5, 22.2, 23.0, 23.5, 24.3, 24.8, 25.7, 26.4, 26.9, 27.3, 28.4, 29.0.

10. The method of claim 3, wherein the organic solvent contains water up to 15% by volume based on the total volume of the organic solvent.

* * * * *